United States Patent [19]

Tos

[11] Patent Number: Plant 7,505

[45] Date of Patent: Apr. 23, 1991

[54] NECTARINE TREE, "LATE RED JIM II"

[75] Inventor: John W. Tos, Hanford, Calif.

[73] Assignee: Tos Farms, Inc., Hanford, Calif.

[21] Appl. No.: 457,159

[22] Filed: Dec. 26, 1989

[51] Int. Cl.[5] ..... A01H 5/00

[52] U.S. Cl. ..... Plt./41

[58] Field of Search ..... Plt./41

[56] References Cited

U.S. PATENT DOCUMENTS

P.P. 4,518 4/1980 Ito ..... Plt. 41

*Primary Examiner*—James R. Feyrer

*Attorney, Agent, or Firm*—Worrel & Worrel

[57] ABSTRACT

A new and distinct variety of nectarine tree which is somewhat remotely similar to the Red Jim nectarine tree (U.S. Plant Pat. No. 4,518) with which it is most closely related but from which it is distinguished in several respects including that of producing fruit which is mature for harvest and shipment later than the Red Jim nectarine tree, or approximately August 30 through September 20 in the San Joaquin Valley of California.

1 Drawing Sheet

1

BACKGROUND OF THE NEW VARIETY

The present invention relates to a new and distinct variety of nectarine tree which will hereinafter be denominated varietally as "Late Red Jim II", and more particularly to such a nectarine tree which produces fruit which is mature for commercial harvesting and shipment approximately August 30 through September 20 in the San Joaquin Valley of central California, and which further is distinguished by producing a clingstone fruit, the flesh of which is very firm and crisp, and which has noteworthy shipping and handling characteristics.

The commercial demand for tree fruit is dependant not only upon the size, color and flavor of the fruit, but as importantly the period of ripening thereof. Enormous effort has been directed toward the development of varieties which produce fruit of commercial quality which ripens early or late in the growing season when there are few or no competing varieties of fruit available for market.

In this regard, the "Red Jim" nectarine tree has been of significant commercial success in that it produces fruit which, when mature, has a high coloration, maintains its attributes well in storage and is particularly well suited for shipping. The fruit of the "Red Jim" matures in early August in the San Joaquin Valley of California with the first picking occurring on or about August 6 and the last picking on or about August 27. It has long been recognized that it would be highly desirable to have a variety of nectarine tree producing fruit having many of the same attributes as the "Red Jim" nectarine tree, but ripening for harvest after the "Red Jim" nectarine tree so that the market for such fruit could be met much later in the season.

ORIGIN AND ASEXUAL REPRODUCTION OF THE NEW VARIETY

The present variety of nectarine tree was discovered by the inventor in an orchard which is located near Hanford, in the San Joaquin Valley of California. The new variety is a mutation of the "Red Jim" nectarine tree and was discovered by the inventor in 1985 in a 40 acre orchard of "Red Jim" nectarine trees of the inventor located adjacent to a residence at 3635 9th Avenue near Hanford, Calif.

2

In 1987, 4 "Red Jim" nectarine trees were grafted to the new variety in a 10 acre orchard of "Red Jim" nectarine trees of the inventor adjacent to the orchard where the discovery of the new variety occurred. The trees have continuously been observed since such asexual reproduction and such observation has confirmed that the new variety is distinct from the "Red Jim" nectarine tree in all of the respects hereinafter set forth.

SUMMARY OF THE NEW VARIETY

The "Late Red Jim II" nectarine tree of the present invention is characterized as to novelty by producing a clingstone fruit which has variable amounts of orange-red to dark cherry red color. Further the fruit produced by the "Late Red Jim II" nectarine tree is ripe for commercial harvesting and shipment approximately August 30 through September 20 in the San Joaquin Valley of central California. The new variety is most closely similar to the "Red Jim" nectarine tree (U.S. Plant Pat. No. 4,518) from which it is believed it was derived as a mutation, but from which it is distinguishable and characterized principally as to novelty by producing fruit which are ripe for harvest and shipment approximately three weeks after the "Red Jim" nectarine tree and which further produces a clingstone fruit having noteworthy shipping and handling characteristics.

The new variety of the present invention additionally is distinguishable from the "Red Jim" nectarine tree in that while the fruit of the "Red Jim" nectarine tree has a very noticeable suture stripe of a narrow band of yellow skin coloration running the length of the ventral suture, that of the instant variety possesses a suture taking on the coloration of the underlying ground color or blush color. The fruit of the new variety also exhibits a different intensity of red coloration than that of the "Red Jim" nectarine tree. Under similar cultural conditions, the fruit of the new variety exhibits a less intense red skin coloration, but a greater glossy fruit finish over that of the "Red Jim" nectarine tree.

BRIEF DESCRIPTION OF THE DRAWINGS

The accompanying drawing is a color photograph of three mature nectarines of the instant variety showing the form and coloration thereof; one mature nectarine sectioned with the stone left in place; one stone of the new variety with the fibers removed therefrom; and characteristic foliage of the new variety showing both the dorsal and ventral surfaces of the leaves.

DETAILED DESCRIPTION

Referring more specifically to the pomological details of this new and distinct variety of nectarine tree, the following has been observed under the ecological conditions prevailing at the orchard of origin which is located near Hanford in the San Joaquin Valley of central California. All major color code designations are by reference to the Dictionary of Color, by Maerz and Paul, Second Edition, 1950.

TREE

Generally:

*Size.*—Large.

*Vigor.*—Moderately vigorous. The tree is hardy as grown under typical climatic conditions in the San Joaquin Valley.

*Figure.*—Upright to upright spreading when trained in a vase shaped system.

*Productivity.*—Productive.

*Regularity of bearing.*—Regular.

Trunk:

*Size.*—Average diameter.

*Surface texture.*—Average with moderate amount of scarfskin present.

*Bark color.*—Grey-brown (15-C-7).

*Lenticels.*—Numbers — numerous. Size — large. Light brown (13-I-9) callous tissue surrounding the lenticel openings.

Branches:

*Size.*—Average.

*Surface texture.*—Average.

*Color.*—One year or older wood — Brown (15-E-9). Immature shoots — Light green (19-J-5) tinged with red coloration on most exposed surfaces.

LEAVES

Leaf measurements were taken from leaves growing on vigorous, upright, current season's shoots.

Size:

*Generally.*—Medium to large.

*Average length.*—17.5 cm including petiole.

*Average width.*—4.7 cm.

Form: Lanceolate, tip form acuminate and often curled downwardly and slightly twisted to one side.

Color:

*Upwardly disposed surface.*—Medium green (24-L-8).

*Downwardly disposed surface.*—Lighter grey-green (21-H-4).

*Leaf vein.*—Yellow (17-I-4).

Marginal form:

*Generally.*—Broadly crenate with wide and shallow crenations.

Leaf vein:

*Thickness.*—1.0 mm in mid leaf.

Leaf margin: Moderately undulate.

Petiole:

*Length.*—Medium, 10 to 12 mm.

*Thickness.*—1.5 to 2.0 mm.

*Color.*—Light yellow-green (18-J-4), more greenish along the petiole groove.

Leaf glands:

*Form.*—Reniform with 3 to 6 glands present. Most frequently 2 to 3 glands are present on the petiole just below the base of the leaf margin and an additional 2 to 3 glands are present on the lower leaf margin.

*Position.*—Alternate.

*Color.*—Shiny yellow (18-K-2) when young, darkening and deteriorating with age.

Stipules: Two stipules are present on young terminal leaves but rapidly become deciduous. Stipules are small, 4 to 5 mm in length with serrate edges.

*Color.*—Yellow-green (18-J-5) when young, darkening with age.

FLOWERS

Bloom described from orchard of propagation near Hanford, Calif. Number of chilling hours recorded in Reedley, Calif. during the 1988–1989 season was 1390 hours. Thus, it was a relatively high chilling year.

Flower buds:

*Size.*—Medium and conic form. One to two buds present per mode, most commonly two.

*Surface texture.*—Heavily pubescent with bud scales greyish-brown (7-C-9).

Flowers:

*Generally.*—Average for large, showy type bloom.

Date of bloom: Mid season in comparison with the bloom of other commercial nectarine cultivars. Full bloom March 11.

Size:

*Generally.*—38 to 42 mm in diameter when fully expanded.

Bloom quantity: Moderate.

Petals:

*Color.*—Pink (1-B-2), darkening to a light rose (1-F-3) basally. Short, truncate claw also colored rose (1-C-4) and becoming darker with age.

Size.—Large, 22 to 24 mm in length, 16 to 18 mm in width.

*Form.*—Somewhat variable, but most commonly ovate. Petal margins undulate, becoming very undulate over the petal apex.

Pedicel: Very short, averaging 1.5 mm in length and 1.5 to 2.0 mm in thickness. Pedicel color bright green (18-K-7).

Nectaries:

*Color.*—Bright orange (11-B-12) darkening and becoming somewhat dull with age.

Anthers: Average in size for species.

*Color.*—Red-orange (4-J-11) dorsally and tan-buff (10-I-6) ventrally.

Pollen: Abundant.

*Color.*—Yellow (10-L-3).

Stamens:

*Size.*—Medium in length, averaging 16 to 18 mm. Slightly shorter than the pistil.

*Color.*—Light pink (1-C-1) when young darkening to rose-violet (1-E-4) with age.

Pistil:

*Size.*—Length 18 to 19 mm, including ovule. Glabrous.

*Color.*—Light green-yellow (18-J-4).

FRUIT

Maturity when described: Ripe for commercial harvesting and shipment approximately August 30 through September 20 near Hanford, Calif. Fruit hangs well on tree for as much as a three week period.

Size:

*Generally.*—Uniform and large.

*Average diameter in the axial plane.*—84 mm.

*Average diameter in the suture plane.*—79 mm.

*Average cheek diameter.*—80 mm.

*Form — uniformity.*—Uniform.

*Form — symmetry.*—Usually slightly asymmetrical. Ovate in lateral aspect. Nearly round in apical aspect.

*Suture — generally.*—A broad distinct groove from apex to base along the ventral surface. Suture somewhat narrower and folded together within the stem cavity.

*Suture — color.*—In most cases the suture takes on the color of the underlying blush or ground coloration of the surrounding fruit surface. There is no distinct suture color stripe. In some cases there is some dark red (6-K-10) striping along the ventral suture and on, or parallel to, the ventral suture where the suture is underlain with red blush color. The ventral suture is more distinct and depressed over the apical shoulder area and next to the apex. The suture is also visible over the apical shoulder of the dorsal surface while being more distinct and depressed near the apex.

*Ventral surface.*—Generally rounded and moderately lipped. Most often one side slightly more lipped and one fruit side slightly larger than the other.

*Stem cavity — generally.*—Medium in size and moderately deep.

*Stem cavity — width.*—Average 27 to 32 mm.

*Stem cavity — depth.*—Average 18 to 20 mm.

*Stem cavity — length.*—Average 29 to 34 mm.

*Stem cavity — shape.*—Oval. On most fruit a branch indentation is present in the basal shoulders where the fruit was tightly attached to the fruiting branch.

*Stem — size.*—Short, from 12 to 14 mm in length. Moderately thick from 4 to 5 mm in diameter.

*Stem — color.*—Greenish-yellow (19-K-1) to light brown (12-H-5).

*Base.*—Rounded. Base angle variable with the base most commonly slightly oblique to the fruit axis.

*Apex.*—Shape — Variable, from rounded to slightly pointed.

*Pistil point.*—Pistil point usually oblique. Distinct depressions are present on each side of the apex on both the dorsal and the ventral suture lines.

Skin:

*Generally.*—Average thickness with mild flavor. Tenacious to flesh at commercial maturity. Glabrous. Bright glossy finish.

*Tendency to crack.*—None observed.

*Color.*—Variable amounts of blush color present from 30 to 90 percent, depending upon the fruit location on the tree and the amount of sun exposure. Color intensity variable from an orange-red (4-F-11) to a dark cherry red (7-L-10). Blush color usually overlain with dark red spotting and dappling (7-J-9). Moderate number of light colored dots present, expecially over apical shoulders.

Flesh:

*Color.*—At commercial maturity, flesh color is a yellow-amber (11-H-6) from the skin inward toward the pit.

*Surface of pit cavity.*—Dark red (7-J-9) with substantial amount of slightly lighter red (6-K-9) coloration radiating out from the pit cavity into the surrounding flesh area.

*Flavor.*—Good, slightly acidic.

*Aroma.*—Slight.

*Texture.*—Firm and crisp at commercial maturity; flesh softens somewhat after harvest.

*Fibers.*—Numerous short, light colored fibers with medium texture.

*Ripening.*—Evenly.

*Eating quality.*—Good.

Stone:

*Attachment.*—Clingstone, held tightly in fruit cavity.

*Fibers.*—Numerous and moderately short.

*Size — length.*—Average 40 to 45 mm.

*Size — width.*—Average 28 to 29 mm.

*Size — thickness.*—Average 21 to 23 mm.

*Form.*—Generally — obovate.

*Color.*—Dry — brown (6-F-10), tinged with purple staining.

*Apex.*—Shape — thin and acute.

*Base.*—Shape — broadly truncate. Base angle variable but most often slightly oblique to stone axis.

*Surface.*—Coarsely grooved and pitted with high ridges, especially over the apical shoulders apically.

*Sides.*—Generally — variable, but most often unequal in size.

*Hilum.*—Large, oval. Margins of hilum surrounded by a raised, heavily grooved and eroded collar.

*Ventral edge.*—Moderately broad with low wings converging apically.

*Dorsal edge.*—Moderately broad with a deep groove extending to only 8 to 12 mm above the stone base. Several coarse ridges occur over the edge at mid-stone, converging basally. The apical shoulder of the dorsal edge usually moderately eroded and at times is concave in this region of the stone.

*Tendency to split.*—No tendency observed.

Use: Fresh market late season nectarine for local market and also suitable for long distance shipping.

Keeping quality: Good.

Although the new variety of nectarine tree possesses the described characteristics noted above as a result of the growing conditions prevailing near Hanford, Calif. in the central part of the San Joaquin Valley, it is to be understood that variations of the usual magnitude and characteristics incident to changes in growing conditions, fertilization, pruning, pest control, irrigation and the like are to be expected.

Having thus described and illustrated my new variety of nectarine tree, what I claim as new and desire to be secured by Plant Letters Patent is:

1. A new and distinct variety of nectarine tree substantially as illustrated and described and which is somewhat remotely similar to the Red Jim nectarine tree (U.S. Plant Pat. No. 4,518) with which it is most closely similar but from which it is distinguished and characterized principally as to novelty by producing fruit which is mature for commercial harvest and shipment approximately August 30 through September 20 in the San Joaquin Valley of California and which further has noteworthy shipping and handling characteristics.

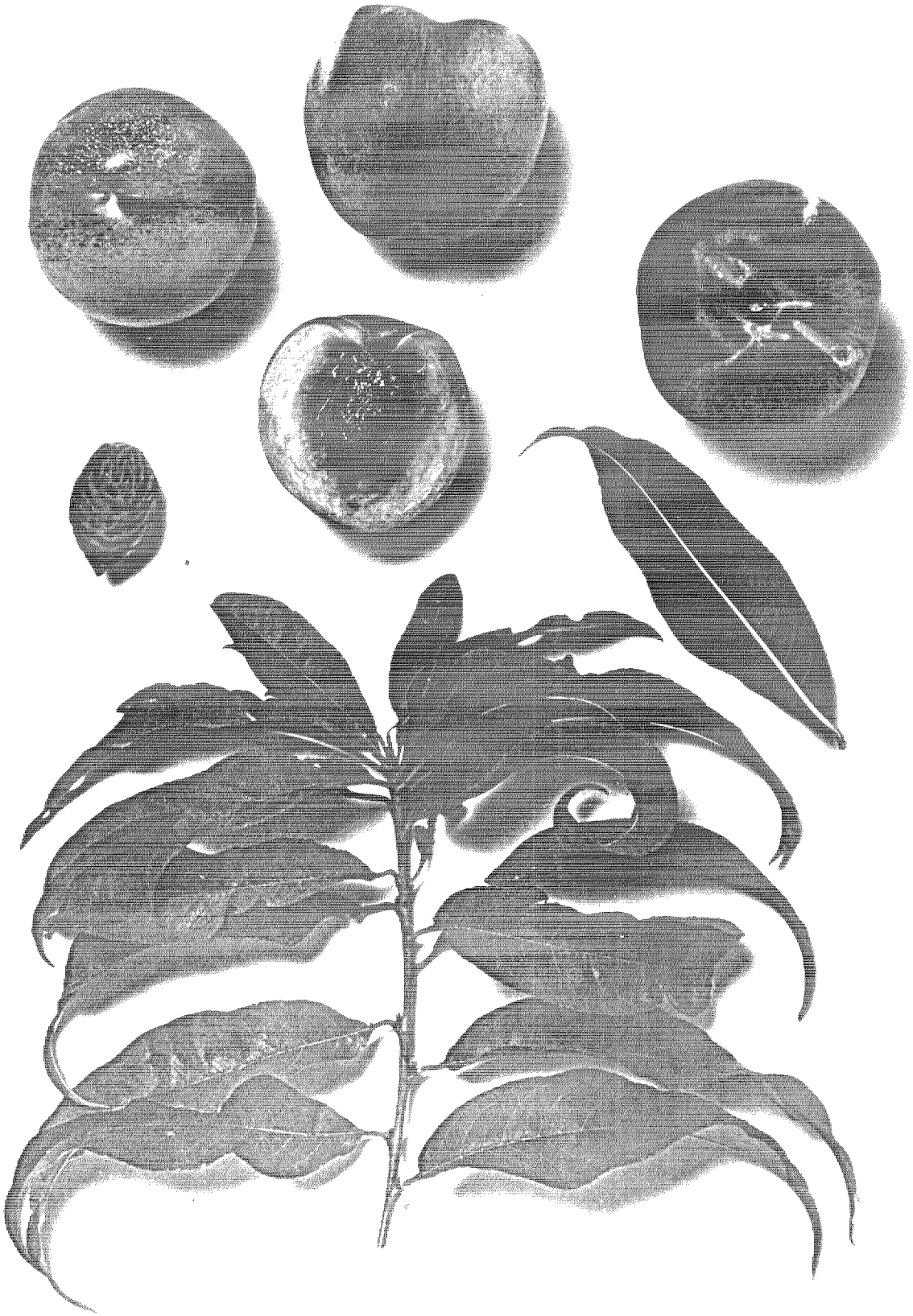

* * * * *